(12) United States Patent
Pokorny

(10) Patent No.: US 9,982,944 B2
(45) Date of Patent: May 29, 2018

(54) PIVOT MECHANISM FOR FURNACE HEAD

(71) Applicant: Ivoclar Vivadent AG, Schaan (LI)

(72) Inventor: Walter Pokorny, Gais (AT)

(73) Assignee: Ivoclar Vivadent AG, Schaan (LI)

( * ) Notice: Subject to any disclaimer, the term of this patent is extended or adjusted under 35 U.S.C. 154(b) by 0 days. days.

(21) Appl. No.: 14/130,520

(22) PCT Filed: Jul. 3, 2013

(86) PCT No.: PCT/EP2013/064012
§ 371 (c)(1),
(2) Date: Jan. 2, 2014

(87) PCT Pub. No.: WO2014/009217
PCT Pub. Date: Jan. 16, 2014

(65) Prior Publication Data
US 2015/0111163 A1    Apr. 23, 2015

(30) Foreign Application Priority Data

Jul. 12, 2012 (EP) ..................................... 12176209

(51) Int. Cl.
| F27D 1/18 | (2006.01) |
| A61C 13/20 | (2006.01) |
| F27B 17/02 | (2006.01) |

(52) U.S. Cl.
CPC .............. *F27D 1/18* (2013.01); *A61C 13/20* (2013.01); *F27B 17/025* (2013.01); *F27D 1/1808* (2013.01)

(58) Field of Classification Search
CPC ........ F27D 1/18; F27D 1/1825; F27D 1/1841; F27D 1/185
See application file for complete search history.

(56) References Cited

U.S. PATENT DOCUMENTS 1,773,049 A * 8/1930 Lobley .................. F27D 1/1858
110/173 R
2,483,968 A * 10/1949 Ecklund ............... C21D 9/0006
110/176

(Continued)

FOREIGN PATENT DOCUMENTS

| CN | 202078414 U | 12/2011 | |
| DE | 4040424 A1 * | 6/1992 | .......... H05B 6/6417 |

(Continued)

OTHER PUBLICATIONS

International Preliminary Report on Patentability of PCT/EP2013/064012, dated Jan. 13, 2015, 8 pages.

*Primary Examiner* — Nathaniel Herzfeld
(74) *Attorney, Agent, or Firm* — Ann M. Knab; Thad McMurray

(57) ABSTRACT

In a dental furnace or dental press furnace comprising a furnace base (14) which is provided with a supporting surface for at least one dental restoration part, a furnace head (12) is provided which is connected to the furnace base (14) via a joint device (16) attached to the furnace base (14) and which is pivotable relative to the furnace base (14) via said device. Pivoting takes place about a pivot axis (40) which extends substantially parallel to the supporting surface, as well as a motor (42) which acts on the joint device (16) for the pivotable movement of the furnace head (12). The pivot axis (40) extends outside of the furnace head (12) and outside of the joint device (16).

14 Claims, 3 Drawing Sheets

(56) References Cited

U.S. PATENT DOCUMENTS

| | | | |
|---|---|---|---|
| 2,506,071 A | | 5/1950 | David |
| 3,343,904 A | * | 9/1967 | Laug ..................... E06B 3/385 |
| | | | 126/191 |
| 4,074,963 A | * | 2/1978 | Walsh .................. F27D 1/1858 |
| | | | 110/173 R |
| 4,139,341 A | * | 2/1979 | Pfaffenbauer ........... F27B 17/02 |
| | | | 432/184 |
| 4,332,553 A | * | 6/1982 | Earle ....................... F27B 5/04 |
| | | | 266/250 |
| 4,817,240 A | * | 4/1989 | Sovis, Jr. ............ E05D 11/1014 |
| | | | 126/194 |
| 4,827,569 A | * | 5/1989 | Mertes ..................... E05D 3/16 |
| | | | 16/288 |
| 5,788,485 A | * | 8/1998 | Grunenfelder ......... A61C 13/20 |
| | | | 432/206 |
| 6,073,624 A | * | 6/2000 | Laurent ................ A47B 46/005 |
| | | | 126/273 A |
| 6,157,004 A | | 12/2000 | Bizzio |
| 8,232,506 B2 | * | 7/2012 | Jussel .................... A61C 13/20 |
| | | | 219/390 |
| 9,492,253 B2 | | 11/2016 | Rohner et al. |
| 2006/0281043 A1 | | 12/2006 | Huffman |
| 2007/0065769 A1 | | 3/2007 | Rohner et al. |
| 2009/0206644 A1 | * | 8/2009 | Ishii .................... B60N 2/0232 |
| | | | 297/362 |
| 2011/0038391 A1 | * | 2/2011 | Miani ..................... F27B 3/085 |
| | | | 373/71 |

FOREIGN PATENT DOCUMENTS

| | | |
|---|---|---|
| DE | 102004049888 A1 | 4/2006 |
| RU | 2098045 C1 | 12/1997 |

\* cited by examiner

PIVOT MECHANISM FOR FURNACE HEAD

CROSS-REFERENCE TO RELATED APPLICATIONS

This application is a National Stage application of International patent application PCT/EP2013/064012 filed on Jul. 3, 2013, which claims priority to European patent application No. 12176209.0 filed on Jul. 12, 2012, the disclosures of which are incorporated herein by reference in their entirety.

The invention relates to a furnace, according to the preamble of claim 1.

Dental furnaces or dental press furnaces are typically provided with a furnace base on which a dental restoration part can be deposited, and a furnace head which is substantially hood-shaped and also carries the heating for the firing chamber.

Dental furnaces comprising a pivotable furnace head have been known for a very long time; exemplary of this is U.S. Pat. No. 569,911.

Considerable progress when it comes to the usability was rendered by the solution according to DE 26 32 846 which stands out due to its flat and smooth supporting surface for the dental restoration part in the furnace base. In the rear part, such solutions are provided with a joint attached between the base and head comprising a pivot axis which proceeds through the pivoting bearing pin of the pivot joint there.

In order to facilitate an easy removal by the dental technician who operates the furnace the head must be pivoted open relatively widely, e.g. at a pivot angle of 35°, as disclosed in DE 195 42 984 C1. In this solution a pin bearing is provided in addition which facilitates an additional lifting by 30 mm whereas this construction is, however, comparably complex.

When a firing cycle has been concluded the furnace is opened by pivoting the furnace head to the top. In this condition, the furnace head is still relatively hot. If possible, it should not remain in an open state for a long time because otherwise it will cool down and must be heated again longer for the next firing cycle. Therefore, it is important that the dental technician can remove the dental restoration parts fast, without a cooling phase being necessary. In order to facilitate this, the dental technicians require the furnace head to be pivoted open widely. However, wide pivoting has, unfortunately, the effect that the operator is irradiated by the hot bottom of the furnace head, which is perceived as inconvenient by the operator, so that sometimes it is recommended to wear protective clothing in order to reduce the danger of burns.

Compared with this, it is the object of the invention to provide for a dental furnace or dental press furnace, according to the preamble of claim 1, which is improved in terms of usability.

This object is inventively solved by claim 1. Advantageous developments may be taken from the subclaims.

According to the present invention, a so-called virtual pivot axis is created using a special joint device, that is, a pivot axis which is outside of the furnace head on the one hand and of the joint device itself on the other hand. For this purpose, the joint device is provided with a leg fixed to the furnace bottom and a leg fixed—or at least attachable—to the furnace head, generally like the dental furnaces known. Between these legs two movable legs are provided, namely on top of each other. These four legs mentioned are connected to each other via four joint axes so that they form a type of parallelogram.

While in a classic furnace joint the pivot axis of the furnace head runs through the joint axis, that is the bearing pin which is provided there in most of the cases, in the present invention the pivot axis extends far outside of the furnace, at that side of the joint device which is opposite the furnace head.

The pivot axis extends horizontally, i.e. parallel to the supporting surface for the dental restoration parts at the furnace base.

Typically, the distance between the pivot axis and the joint device corresponds approximately to the diameter of the furnace head.

According to the invention, the furnace can in this way be pivoted open widely at a comparatively small pivot angle for the removal of the dental restoration parts. The distance between the furnace head and the dental restoration parts is larger in spite of the smaller pivot angle, and the operator is barely irradiated by the hot bottom of the furnace head. Rather, the heat radiates to the bottom so that it remains in the furnace area, and upon fast removal only little heat is lost.

According to the invention, it is favorable that the joint device can be produced compactly and surprisingly cheaply. The legs of the joint device can be realized cheaply as punched parts. Preferably, the joint device consists of two joint arrangements which are spaced apart from each other and which are symmetrical to one another. Between these, a tension spring can be received which serves to compensate for the weight of the furnace head as well as the drive motor for the electromotive actuation of the furnace head. Surprisingly, a more compact joint device, compared to the furnace joints known, can be realized in this way.

In an advantageous development it is provided that the joint device comprises at least three, in particular four, legs which are connected to each other via joints and that between adjacent legs a first, a second, a third and in particular a fourth joint axis is formed.

In an advantageous development it is also provided that the joint device comprises several legs, one of which, the frame leg, is firmly connected to the furnace base, and to another one, the head leg, the furnace head can be attached or is attached.

In a further advantageous development it is provided that the joint device comprises several legs and that a head leg which is connected to the furnace head is formed as the leg facing the furnace head.

In a further advantageous development it is provided that the joint device is provided with several legs which are connected to each other via joints and that a frame leg which is fixed to the base is connected via joints to two intermediate legs wherein the joint axes are spaced apart from each other towards them, in particular spaced apart in a vertical direction, and that the other joint axes of the intermediate legs are connected to a leg which is fixed to the furnace head.

In a further advantageous development it is provided that the joint device is provided with two joint arrangements spaced apart from each other in a horizontal direction and in particular spaced apart from each other in the direction parallel to the pivot axis and provided with several legs each.

In a further advantageous development it is provided that between the joint arrangements of the joint device the motor is received which is used to pivot the furnace head.

In a further advantageous development it is provided that in or at the joint device a tension spring is received which acts against the weight of the furnace head and which substantially compensates for this in a way known.

In a further advantageous development it is provided that the tension spring consists of two individual tension springs which are received in the interior of the joint device, in particular between the arrangements of the joint device.

In a further advantageous development it is provided that the joint device is provided with several legs which are connected to each other in the form of a convex square.

In a further advantageous development it is provided that the furnace head is releasably connected to the joint device and the fixing is carried out using pluggable molded parts which are secured via a spring-loaded locking nose.

In a further advantageous development it is provided that a molded part fixed to the furnace head has substantially the shape of a U turned upside down whose side legs end in angular faces.

In a further advantageous development it is provided that a driven shaft of the motor is formed as a spindle and interacts with a worm gear which for its part drives the joint device.

In a further advantageous development it is provided that the distance of the pivot axis to the housing of the furnace is 0.1 to 2 times the largest length of the furnace housing and/or the opening angle between the bottom of the furnace head and the top of the furnace base is 5° to 20° when the furnace head is open.

Further advantages, details and features may be taken from the following description of several embodiments of the invention with respect to the drawings.

Figure 1:
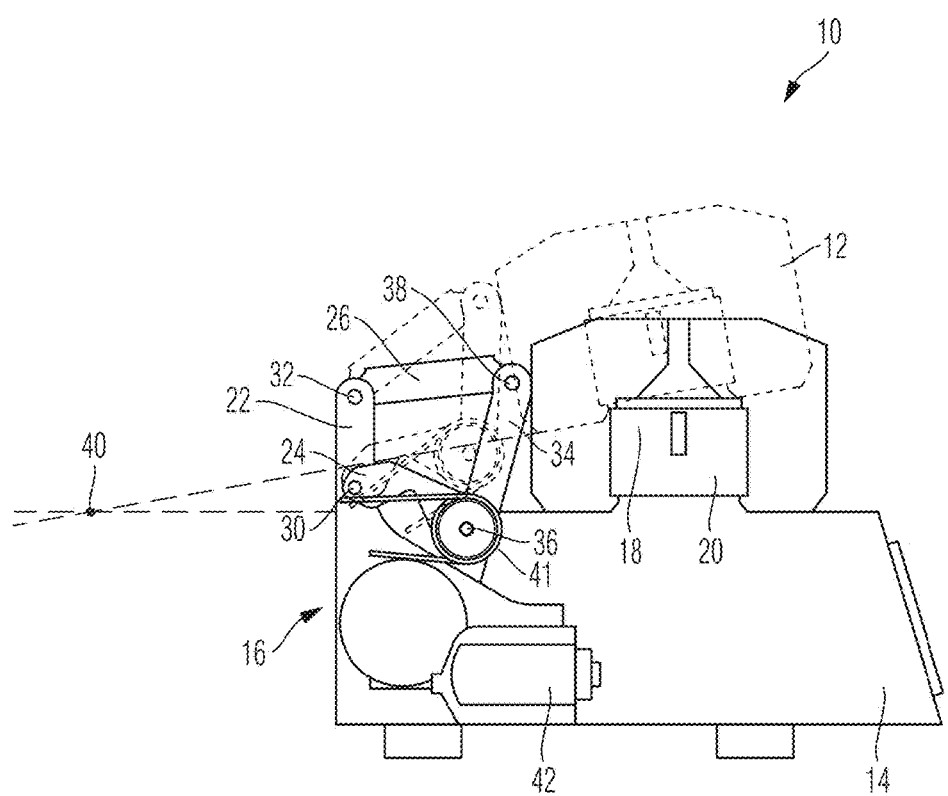
FIG. 1 shows a schematic view of an inventive press furnace in one embodiment.

The inventive furnace or press furnace 10 illustrated in FIG. 1 is formed as a press furnace in this embodiment. It is provided with a furnace head 12 and a furnace base 14 which are connected to each other via a joint device 16. The furnace head 12 comprises, in a way known, a firing chamber 18 which is intended for receiving a muffle 20.

The joint device 16 is inventively formed in a special manner and comprises a frame leg 22 which is connected to the furnace base 14, a lower movable leg 24 and an upper movable leg 26. Both the legs 24 and 26 are each connected via joint axes 30 and 32 to the frame leg 22.

The joint device 16 is further provided with a head leg 34 which is connected via joint axes 36 and 38 to the movable leg 24 or the movable leg 26. The head leg 34 is connected to the furnace head 12, and, in fact, in the illustrated first embodiment it is firmly connected.

In the illustration according to FIG. 1 the open position as well as the closed position of the furnace head 12 are shown on top of each other.

Using the inventive joint device 16, the furnace head 12 is pivotable about a virtual pivot axis 40 which lies considerably spaced apart from the furnace 10. By realizing this virtual pivot axis, a relatively small pivot angle of only about 18° is the result, even when the furnace head 12 is open.

In the area of the joint device 16 a tension spring 41 is mounted. The tension spring preloads the head leg 34 to the top and serves to compensate for the weight of the furnace head so that a motor 42 with a comparatively low driving force by means of the driving shaft which is formed as a spindle and further by means of a worm gear which is connected thereto can open and close the furnace head 12.

Figure 2:
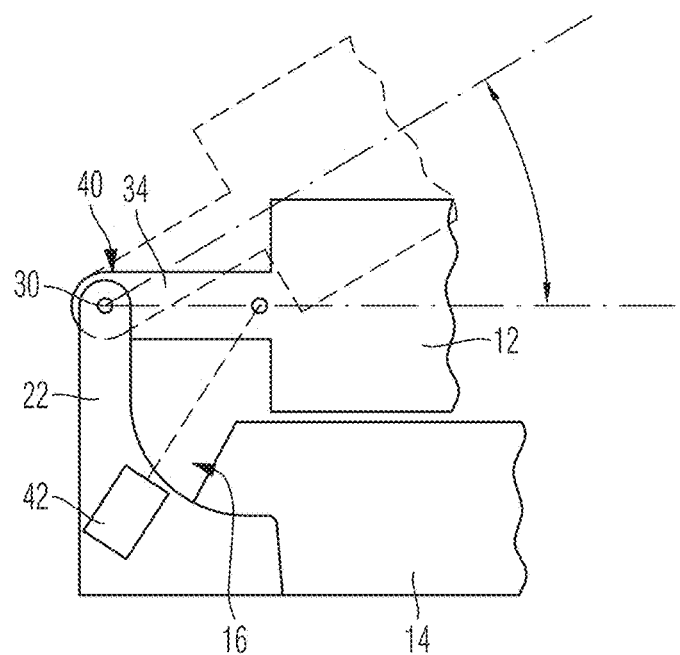
FIG. 2 shows a schematic view of a detail of a conventional furnace illustrating the joint device.

FIG. 2 schematically shows a joint device of a conventional furnace. Here as well as in the further figures, the same reference numbers designate the same parts. Here, the pivot axis 40 concurs with the joint axis 30, and the frame leg 22 is directly connected to the head leg 34 via the joint axis 30. A motor 42 is arranged laterally next to the joint device 16 and acts with a spindle onto the head leg 34.

Figure 3:
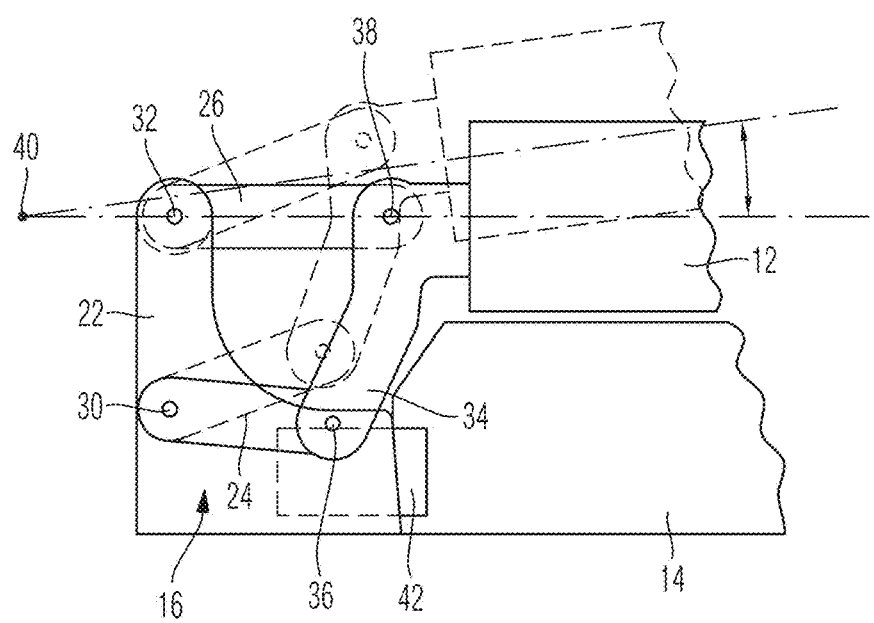
FIG. 3 shows a schematic illustration of a detail of an inventive furnace in a further embodiment, also illustrating the joint device.

In contrast, FIG. 3 shows an inventive joint device 16. The illustration shows the closed position of the furnace head as a solid line and the open position as a dotted line. The embodiment of the joint device in the form of a convex square with the joint axes 30, 32, 36, 38 as corners of the square is clearly visible from FIG. 3. While the pivot axis 40 is presented only slightly outside of the furnace in the view according to FIG. 3, it is to be understood that the actual dimensioning rather corresponds to FIG. 1.

The joint device 16 is shown in FIG. 1 and FIG. 3 in simple form.

In a modified embodiment, the joint device 16 consists of two joint arrangements which are symmetric to each other and correlate each other. In front or behind the drawing layer, in addition to the joint arrangement illustrated, a further corresponding joint arrangement is shown so that both the joint arrangements which are spaced apart from each other in the direction of the pivot axis overall form the joint arrangement 16.

Hereby, the movable legs 24 and 26 are provided preferably twice and the frame leg 22 has the shape of a U so that the center leg of the U extends vertically and the side legs of the U each receive both the joint axes 30 and 32.

The same holds true for the head leg 34 which also connects both joint arrangements to each other and which has substantially the shape of a U in the horizontal section, too. Here, the joint axes 36 and 38 also extend into the side leg of the U. Between the frame legs 30, 32 the motor 42 is received so that altogether a very compact structure of the joint device 16 is achieved.

Figure 4:
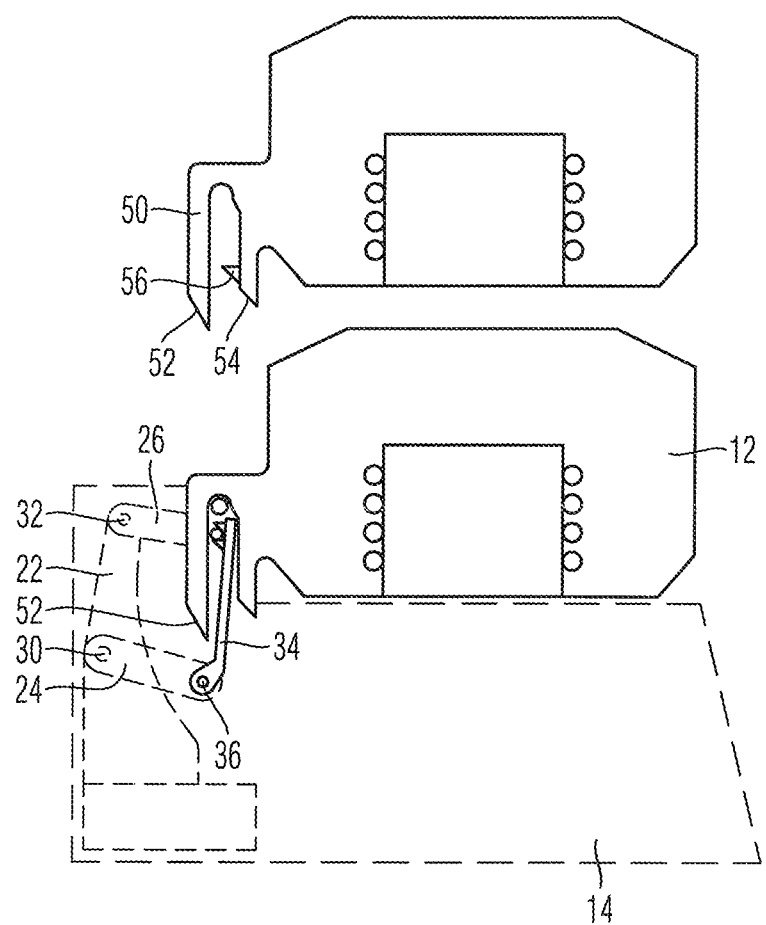
FIG. 4 shows an illustration of a further embodiment of an inventive furnace.

FIG. 4 shows a further modified embodiment of an inventive furnace. Here, too, the head leg 34 extends substantially vertically when the furnace head 12 is closed. However, it is not directly connected to the furnace head 12. Rather, a molded part 50 is provided which is firmly connected to the furnace head 12 and has substantially the shape of a U turned upside down. Its side legs end in angular faces 52, 54 which form insertion slants relative to the head leg 34, and overlap it.

For the locking between the head leg 34 and the molded part 50 a locking nose 56 is provided which is movably mounted at the molded part 50 and which passes through a corresponding opening in the head leg 34 in a locked position in order to, in this way, facilitate a secure connection between the head leg 34 and the furnace head 12.

The invention claimed is:

1. Dental furnace or dental press furnace comprising
   a furnace base provided with a supporting surface for at least one dental restoration part,
   a furnace head connected to the furnace base via a joint device attached to the furnace base and wherein the furnace head is pivotable relative to the furnace base via said joint device,
   wherein pivoting takes place about a range of pivot axes which extend substantially parallel to the supporting surface, a motor which acts on the joint device for the pivotable movement of the furnace head, wherein the range of pivot axes extend outside of the furnace head and outside of the joint device, wherein the furnace head moves initially in an upward direction and subsequently pivots, wherein the furnace head is releasably connected to the joint device and the attachment of the furnace head to the joint device comprises pluggable molded parts, and wherein in or at the joint device a tension spring is received which acts against the weight of the furnace head and which serves to compensate for the weight of the furnace head.

2. Furnace according to claim 1, wherein the joint device comprises at least three legs which are connected to each other via joints and that between adjacent legs a first, a second, a third are formed.

3. Furnace according to claim 1, wherein the joint device comprises several legs, one of which is firmly connected to the furnace base, and to another one the furnace head is attached.

4. Furnace according to claim 1, wherein the joint device comprises several legs and wherein a head leg is connected to the furnace head and is formed as the leg facing the furnace head.

5. Furnace according to claim 1, wherein the joint device is provided with several legs which are connected to each other via joints and wherein a frame leg is fixed to the base and is connected via joints to two intermediate legs wherein first and second joint axes between the two intermediate legs are spaced apart from each other in a vertical direction, and wherein third and fourth joint axes of the two intermediate legs are connected to a fourth leg which is fixed to the furnace head.

6. Furnace according to claim 1, wherein the joint device is provided with two joint arrangements spaced apart from each other in a horizontal direction and spaced apart from each other in a direction parallel to the pivot axis and wherein the joint arrangements are each provided with several legs.

7. Furnace according to claim 6, wherein between the joint arrangements of the joint device the motor is received which is used to pivot the furnace head.

8. Furnace according to claim 7, characterized in that the tension spring comprises two individual tension springs which are received in the interior of the joint device between the arrangements of the joint device.

9. Furnace according to claim 1, wherein the joint device is provided with several legs which are connected to each other in the form of a convex square.

10. Furnace according to claim 1, wherein a molded part fixed to the furnace head has substantially the shape of a U turned upside down with side legs ending in angular faces.

11. Furnace according to claim 1, characterized in that a drive shaft of the motor is formed as a spindle and interacts with a worm gear which in turn drives the joint device.

12. Furnace according to claim 1, wherein the distance of the pivot axis to the furnace head is 0.1 to 2 times a largest length of the furnace head and/or the opening angle between the bottom of the furnace head and the top of the furnace base is 5° to 20° when the furnace head is open.

13. Furnace according to claim 1, wherein the joint device (16) comprises at least four legs which are connected to each other via joints and that between adjacent legs a first, a second, a third and a fourth joint axis are formed.

14. Furnace according to claim 1, wherein the joint device (16) comprises several legs, wherein a frame leg is firmly connected to the furnace base, and a head leg is connected to the furnace head.

* * * * *